(12) United States Patent
Okada

(10) Patent No.: US 7,588,580 B2
(45) Date of Patent: Sep. 15, 2009

(54) MUCOSA EXCISION DEVICE USING ENDOSCOPE

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 463 days.

(21) Appl. No.: 10/724,812

(22) Filed: Dec. 1, 2003

(65) Prior Publication Data
US 2004/0210111 A1 Oct. 21, 2004

(30) Foreign Application Priority Data
Dec. 2, 2002 (JP) .............................. 2002-350228
May 29, 2003 (JP) .............................. 2003-152971

(51) Int. Cl.
*A61B 17/26* (2006.01)
*A61B 1/04* (2006.01)
*A61B 1/00* (2006.01)

(52) U.S. Cl. ..................... 606/113; 600/127; 600/104; 600/106

(58) Field of Classification Search ............... 606/113, 606/114, 170; 600/565, 104, 106, 127
See application file for complete search history.

(56) References Cited

U.S. PATENT DOCUMENTS 5,968,056 A * 10/1999 Chu et al. ............... 606/140
6,068,603 A * 5/2000 Suzuki ...................... 600/565
6,306,081 B1 * 10/2001 Ishikawa et al. ............ 600/127
6,517,539 B1 * 2/2003 Smith et al. ................ 606/47

FOREIGN PATENT DOCUMENTS

| JP | 64-54502 | 4/1989 |
|---|---|---|
| JP | 6-75402 | 10/1994 |
| JP | 8-47360 | 2/1996 |
| JP | 9-66019 | 3/1997 |
| JP | 9-140306 | 6/1997 |
| JP | 9-187415 | 7/1997 |
| JP | 10-286224 | 10/1998 |
| JP | 2001-275933 | 10/2001 |
| JP | 2002-45369 | 2/2002 |

* cited by examiner

*Primary Examiner*—Todd E Manahan
*Assistant Examiner*—Diane Yabut
(74) *Attorney, Agent, or Firm*—Scully, Scott, Murphy & Presser, P.C.

(57) ABSTRACT

In a mucosa excising device using an endoscope according to the present invention, engagement pieces are provided in the vicinity of a claw portion formed at an end edge of a cap, the engagement pieces press the snare wire arranged along the claw portion, both the claw portion and the engagement pieces hold the snare wire, and the snare wire of a high-frequency snare is prevented from accidentally coming off at the time of insertion into a body cavity or during a treatment in the body cavity when conducting endoscopic mucosal resection.

17 Claims, 11 Drawing Sheets

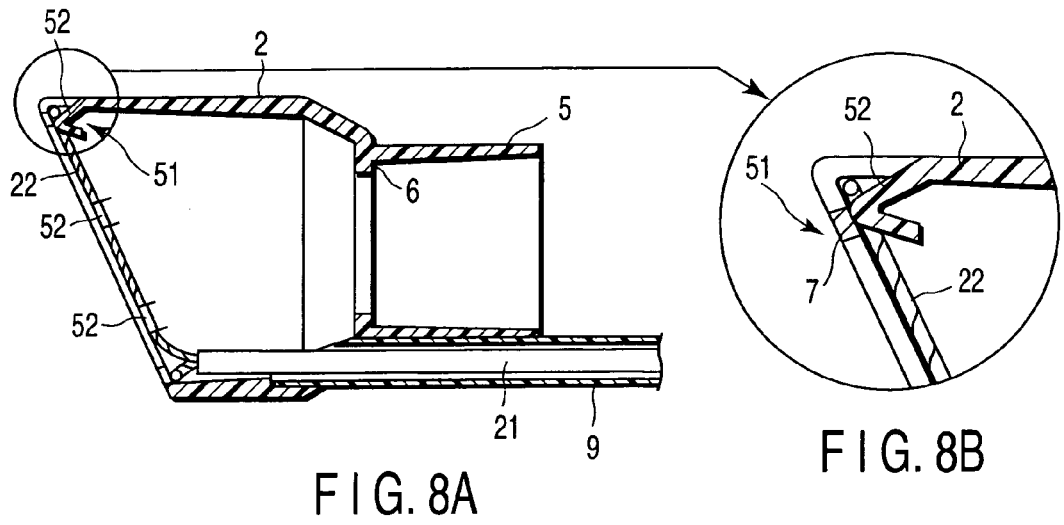
FIG. 8A
FIG. 8B
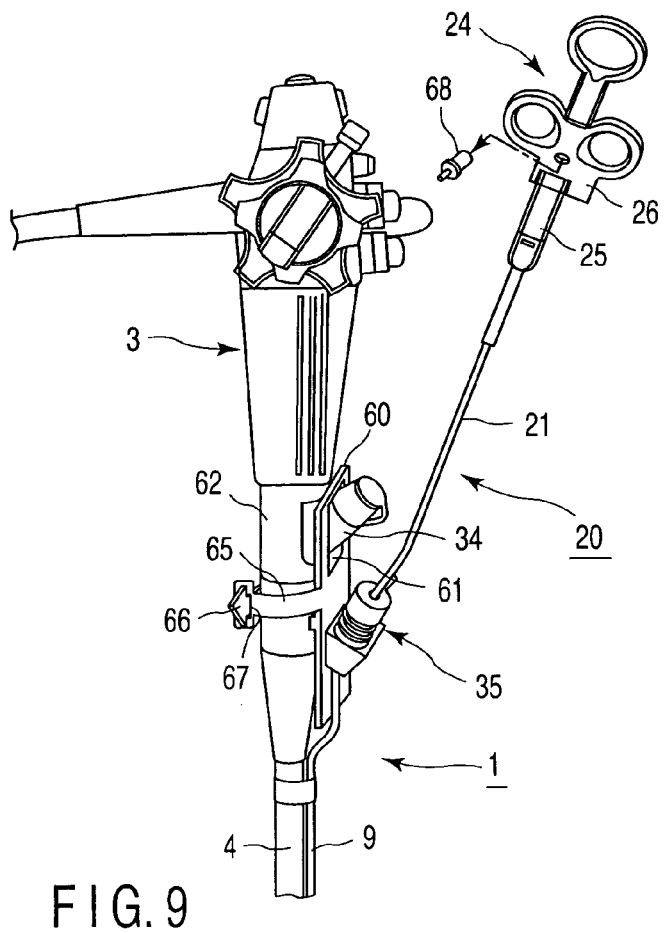
FIG. 9

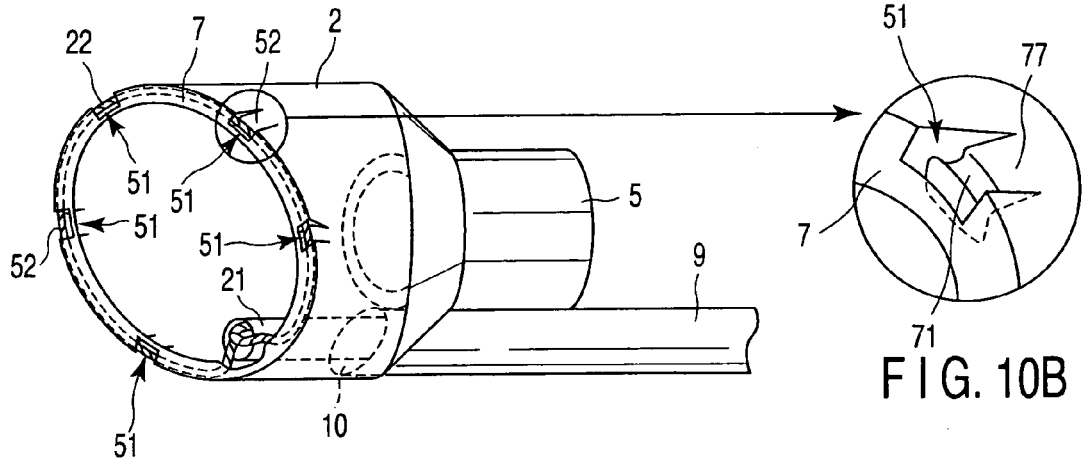
FIG. 10A
FIG. 10B
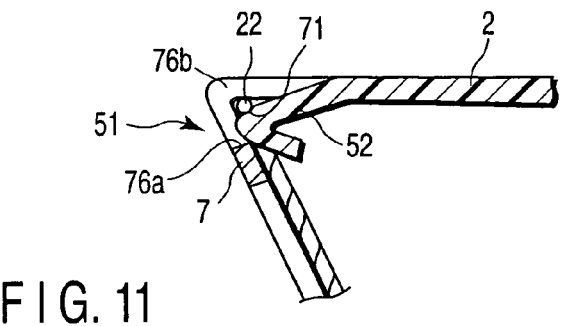
FIG. 11
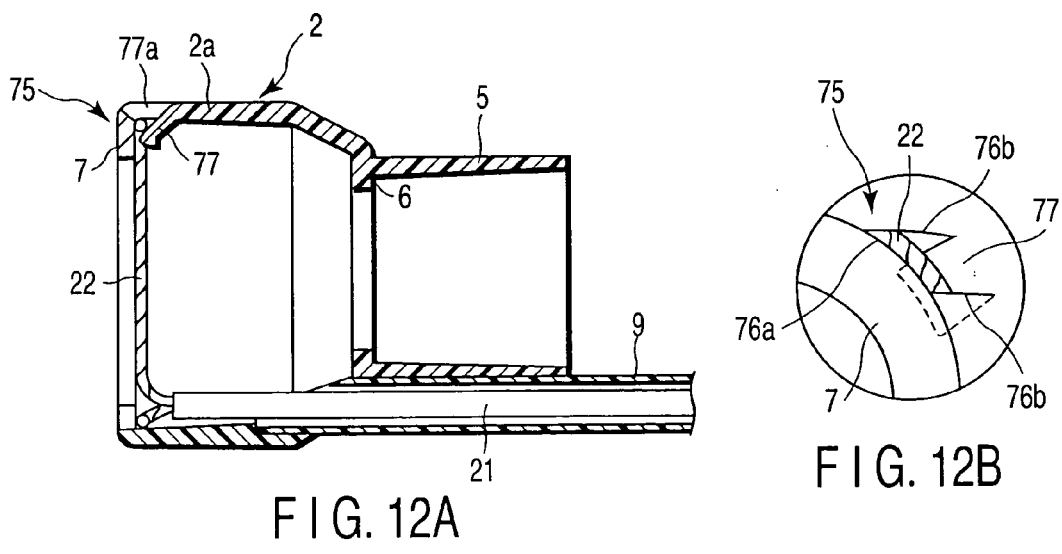
FIG. 12A
FIG. 12B

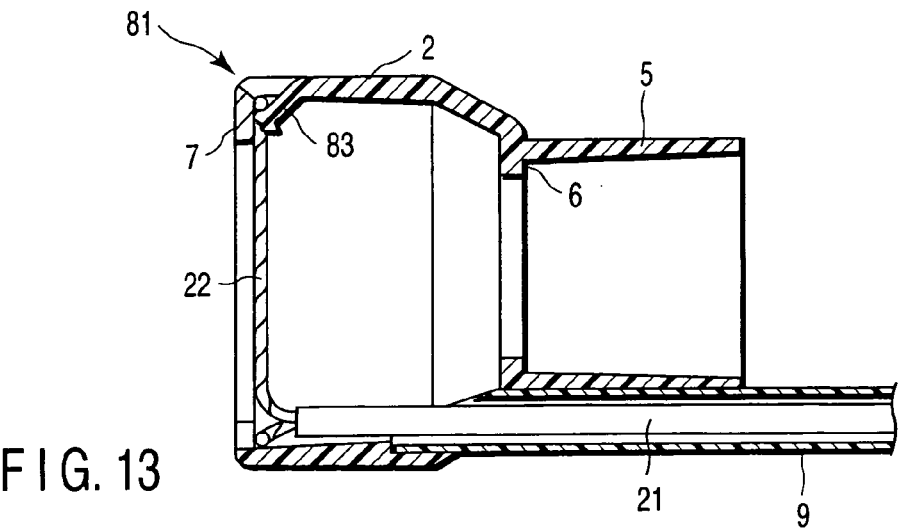
F I G. 13
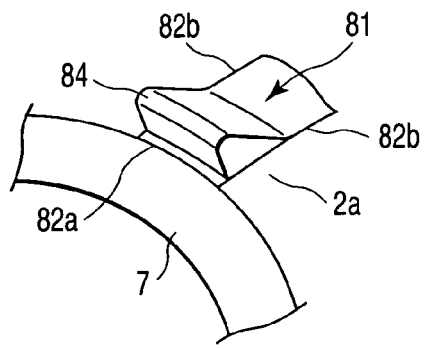
F I G. 14
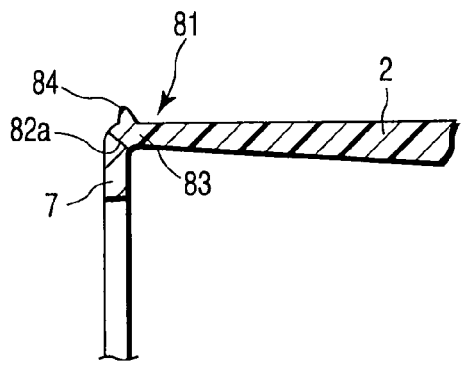
F I G. 15A
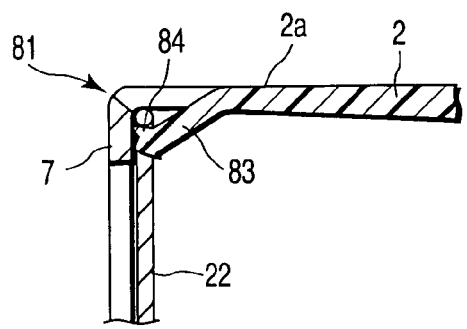
F I G. 15B

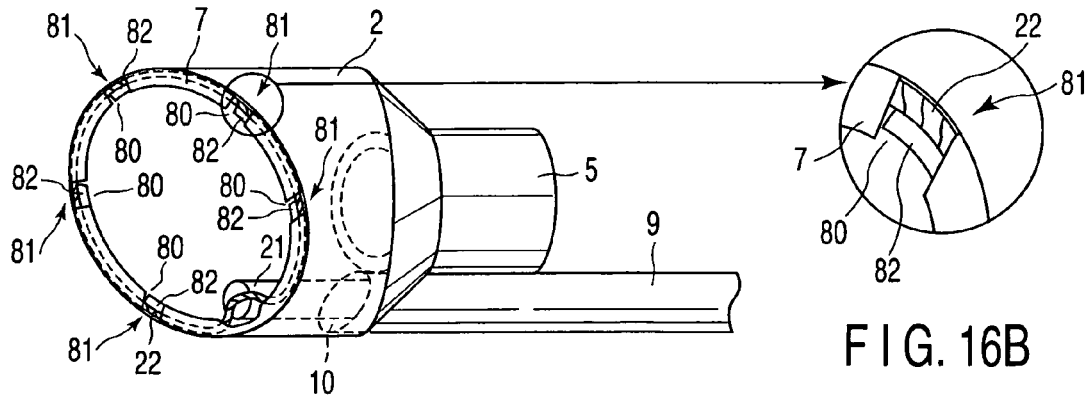
FIG. 16A
FIG. 16B
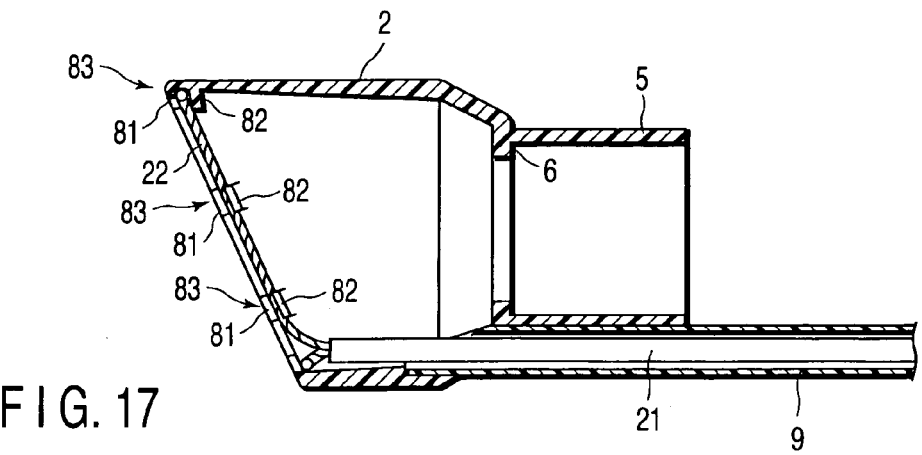
FIG. 17
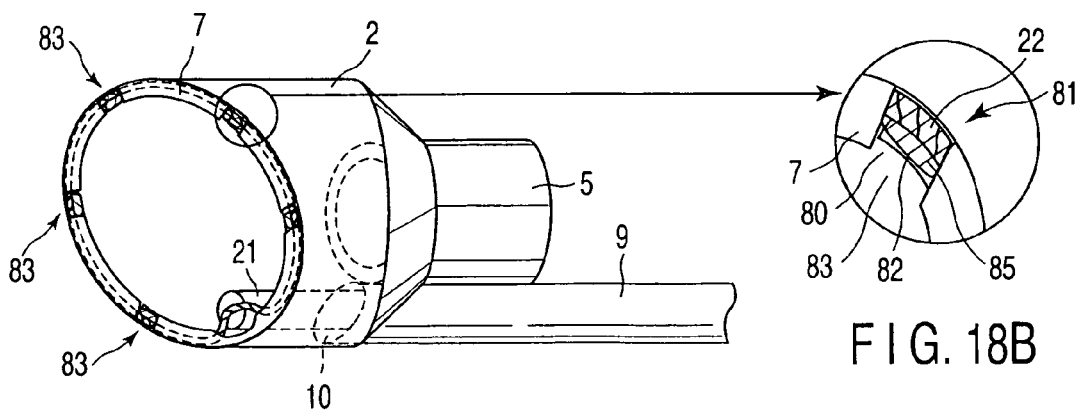
FIG. 18A
FIG. 18B

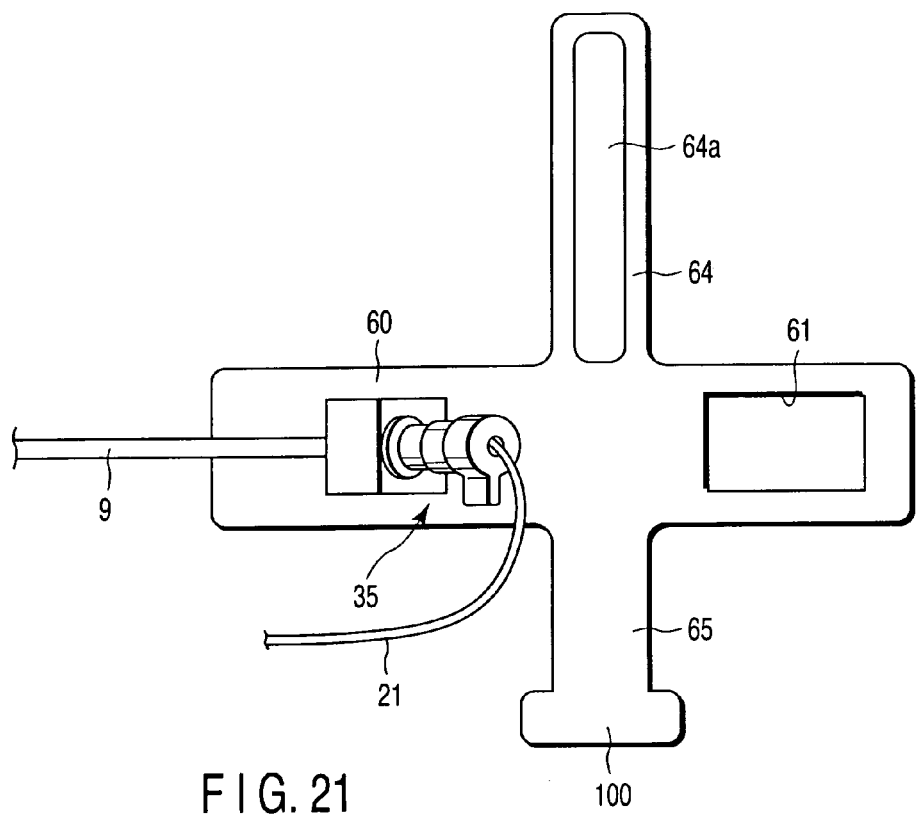
F I G. 21
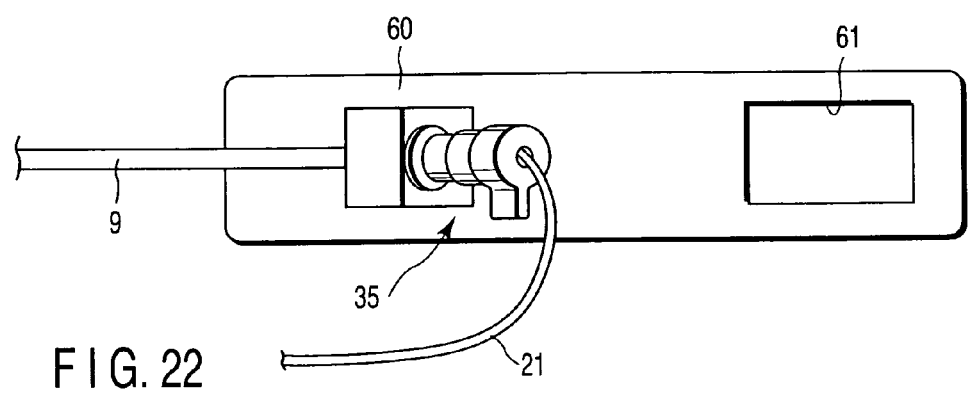
F I G. 22
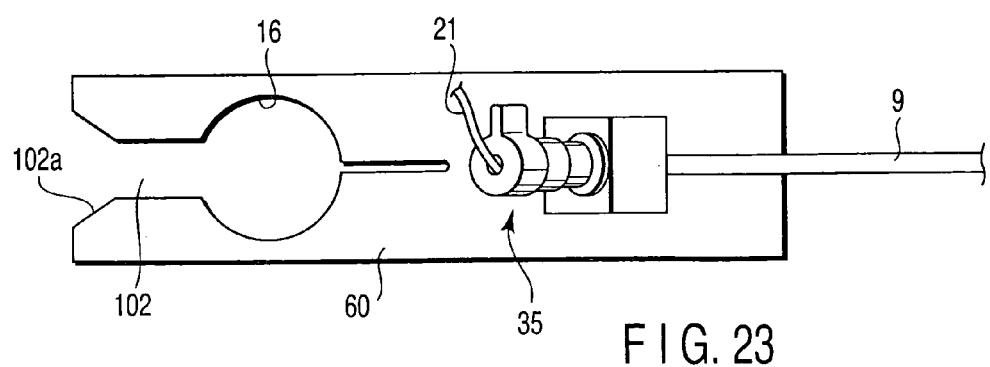
F I G. 23

MUCOSA EXCISION DEVICE USING ENDOSCOPE

CROSS-REFERENCE TO RELATED APPLICATIONS

This application is based upon and claims the benefit of priority from the prior Japanese Patent Applications No. 2002-350228, filed Dec. 2, 2002; and No. 2003-152971, filed May 29, 2003, the entire contents of both of which are incorporated herein by reference.

BACKGROUND OF THE INVENTION

1. Field of the Invention

The present invention relates to a mucosa excising device using an endoscope which sucks a mucosa into a cylindrical cap (which is also referred to as a hood) attached to an end of an insertion portion of the endoscope and excises a polypous base part of the mucosa by using a high-frequency snare.

2. Description of the Related Art

In recent years, there has been conducted an endoscopic mucosal resection which excises a mucosa at a diseased part by using an endoscope without performing a laparotomy with respect to an esophageal or gastric cancer at an early stage. As one of such methods, there is known a method disclosed in Jpn. UM Appln. KOKAI Publication No. 6-75402 and Jpn. Pat. Appln. KOKAI Publication No. 2001-275933. This method conducts an endoscope mucosal resection using a high-frequency snare by secondarily utilizing a cap attached to an end of an insertion portion of an endoscope. In such a method, an end of a snare sheath of the high-frequency snare is led into the cap attached to the end of the insertion portion of the endoscope through a channel of the endoscope, a snare wire is caused to protrude from this end, and a loop of the protruding snare wire portion is formed over an inner part of a claw portion formed on the entire periphery of the end edge of the cap (which will be referred to as a looping operation hereinafter). The mucosa is sucked into the cap, then a base portion of the mucosa is constricted by using the looped wire portion of the high-frequency snare, and the high-frequency snare is energized in order to excise the mucosa.

There is known a method which conducts an endoscopic mucosal resection without requiring the looping operation in a body cavity as disclosed in Jpn. Pat. Appln. KOKAI Publication No. 9-187415 and Jpn. Pat. Appln. KOKAI Publication No. 9-66019. In this method, a wire loop of a high-frequency snare is previously engaged on an outer periphery of a cap in the form of a loop outside the body, and a looped wire portion is inserted into the body.

Further, there is also known a method such as disclosed in Jpn. Pat. Appln. KOKAI Publication No. 2002-45369. In this method, the snare wire is looped along the inside of a claw portion formed over the entire periphery of the end edge of the cap, and it is fixed by means of an adhesive.

BRIEF SUMMARY OF THE INVENTION

In particular, a mucosa excising device using an endoscope according to a first aspect of the present invention comprises:
a substantially cylindrical cap having a circular end portion including a holding mechanism which holds an end portion of a snare wire in a loop form; and
an attachment portion which attaches the cap to an end portion of an endoscope,
wherein the holding mechanism has a plurality of engagement portions which are provided in the vicinity of an end edge of the cap and distanced from each other in a circumferential direction, and each engagement portion has an engagement piece and a corresponding portion which hold the snare wire therebetween.

In the mucosa excising device using an endoscope having such a structure, the loop can be prevented from coming off an engagement position relative to the cap by reviewing the loop engagement with respect to the cap.

A mucosa excising device using an endoscope according to another aspect of the present invention comprises: a substantially cylindrical cap having a flange-shaped protrusion portion which inwardly protrudes from an inner peripheral surface in the vicinity of an end edge; and an attachment portion which attaches the cap to an end portion of an endoscope, a snare wire of a high-frequency snare being expanded and arranged in a loop form along the protrusion portion, wherein an engagement portion is provided at least at a part of the cap in the vicinity of the end edge, the engagement portion has an engagement piece which presses the snare wire arranged along the protrusion portion, and the snare wire is held by the protrusion portion and the engagement portion.

This mucosa excising device using an endoscope includes one having an engagement portion integral with a member of the cap, the engagement portion being formed by notching a wall portion of the cap in the vicinity of the end edge.

With this structure, when conducting an endoscopic mucosal resection, the loop of the high-frequency snare hardly comes off a predetermined position arranged on the cap at the time of insertion into a body cavity or during a treatment in a body cavity in particular.

Moreover, the present invention includes a mucosa excising device using an endoscope, comprising a flexible tube whose opening on an end side communicates with an inner side of the cap, and which is arranged outside an insertion portion of the endoscope when the cap is attached to the endoscope, and used to insert a high-frequency snare, and fixing means which fixes a sheath of the high-frequency snare so as to be capable of being released is provided in the vicinity of a base end portion of the flexible tube.

With such a structure, since the snare sheath inserted into the flexible tube can be prevented from being moved, the loop of the high-frequency snare hardly comes off a predetermined position where it is attached on the cap.

Additionally, a mucosa excising device using an endoscope according to still another aspect of the present invention comprises: a substantially cylindrical cap; an attachment portion which attaches the cap to an end portion of the endoscope; and a flexible tube whose end opening communicates the inner side of the cap, which is arranged outside an insertion portion of an endoscope when the cap is attached to the endoscope, and used to insert a snare sheath of a high-frequency snare, the snare wire of the high-frequency snare inserted into the cap through the flexible tube being expanded and arranged in the cap, wherein fixing means for fixing the snare sheath of the high-frequency snare so as to be capable of being released is provided in the vicinity of a base end portion of the flexible tube.

Since a movement of the snare sheath inserted into the flexible tube can be avoided by using this fixing means, the loop of the high-frequency snare arranged in the cap hardly comes off a predetermined position.

Objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8A is a vertical cross-sectional view showing the cap of the mucosa excising device using an endoscope according to the second embodiment, and FIG. 8B is an enlarged cross-sectional view showing a part surrounded by a circle in FIG. 8A;

FIG. 9 is a perspective view showing the mucosa excising device using an endoscope according to the second embodiment in a use state that it is attached to an endoscope;

FIG. 10A is a perspective view showing a cap of a mucosa excising device using an endoscope according to a third embodiment and its vicinity, and FIG. 10B is an enlarged cross-sectional view showing an engagement portion surrounded by a circle in FIG. 10A;

FIG. 11 is an enlarged vertical cross-sectional view of the engagement portion depicted in FIG. 10B;

FIG. 12A is a perspective view showing a cap of a mucosa excising device using an endoscope according to a fourth embodiment and its vicinity, FIG. 12B is an enlarged perspective view of an engagement portion formed on the cap;

FIG. 13 is a vertical cross-sectional view showing a cap of a mucosa excising device using an endoscope according to a fifth embodiment and its vicinity;

FIG. 14 is a perspective view of an engagement portion formed on the cap depicted in FIG. 13;

FIGS. 15A and 15B are vertical cross-sectional views of an engagement portion of the mucosa excising device using an endoscope according to the fifth embodiment, in which FIG. 15A shows a state before supporting a snare wire and FIG. 15B shows a state supporting the snare wire;

FIG. 16A is a perspective view showing a cap of a mucosa excising device using an endoscope according to a sixth embodiment and its vicinity, and FIG. 16B is an enlarged perspective view of an engagement portion formed on the cap surrounded by a circle in FIG. 16A;

FIG. 17 is a vertical cross-sectional view showing the cap of the mucosa excising device using an endoscope according to the sixth embodiment and its vicinity;

FIG. 18A is a perspective view showing a cap of a mucosa excising device using an endoscope according to a seventh embodiment and its vicinity, and FIG. 18B is an enlarged perspective view of an engagement portion formed on the cap surrounded by a circle in FIG. 18A;

FIG. 21 is a plane view showing a second modification of a hook portion (engagement portion) provided on a base end side of a flexible tube;

FIG. 22 is a plane view showing a third modification of a hook portion (engagement portion) provided on a base end side of a flexible tube; and FIG. 23 is a plane view showing a fourth modification of a hook portion (engagement portion) provided on a base end side of a flexible tube;

DETAILED DESCRIPTION OF THE INVENTION

First Embodiment

A mucosa excising device using an endoscope according to a first embodiment of the present invention will now be described with reference to FIGS. 1A and 1B through FIGS. 4A to 4C.

Figure 3:
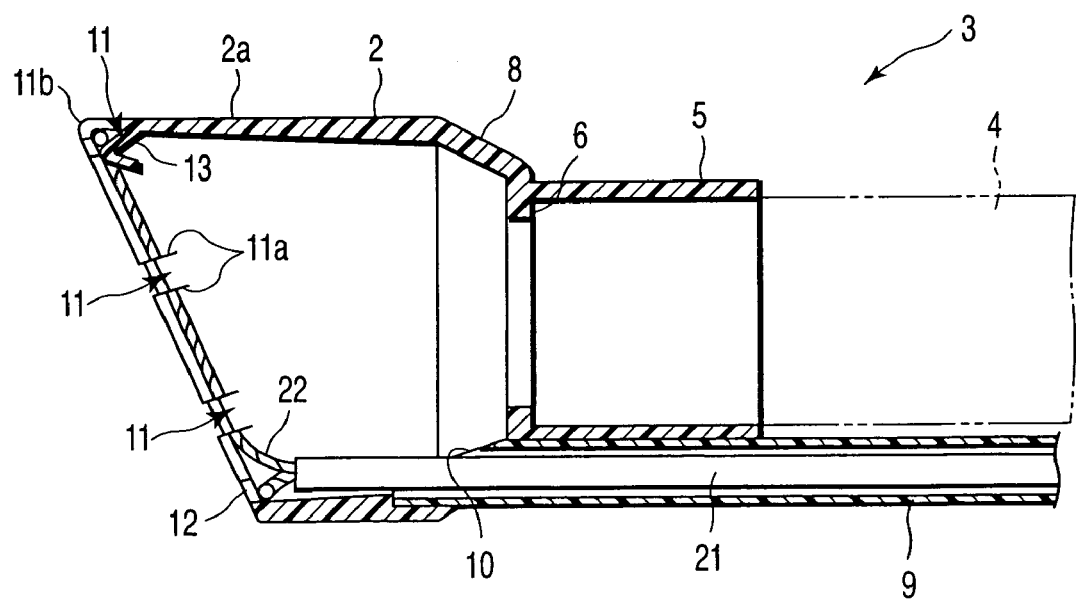
FIG. 3 is a vertical cross-sectional view of the cap depicted in FIG. 2.

FIG. 1A shows an entire mucosa excising device using an endoscope 1, according to this embodiment. This mucosa excising device using an endoscope 1 is externally attachable/detachable with respect to an endoscope, and is a device as a unit independent from the endoscope. The mucosa excising device 1 has a substantially cylindrical transparent cap 2 connected to an end of a later-described flexible tube 9. The cap 2 is formed of, e.g., a transparent synthetic resin so as to be entirely deformable. However, it may not be transparent, nor formed of a synthetic resin, nor elastically deformable. The cap 2 is preferably formed by using an electrical insulator. To the cap 2 is provided a substantially cylindrical endoscope attachment portion 5 which can be detachably disposed at an end part of an insertion portion 4 of a later-described endoscope 3 as an attachment portion which attaches the cap at the end part of the insertion portion 4. As shown in FIG. 3, the attachment portion 5 has a smaller diameter than that of the cap 2 and is integrally formed so as to be continuous to a rear end of the cap 2, and the endoscope attachment portion 5 and the cap 2 are substantially coaxially arranged. Preferably, the attachment portion 5 is integrally formed of the same material as that of the cap 2. For example, it is molded by using a synthetic resin.

As shown in FIG. 3, a flange-like endoscope engagement portion 6 which protrudes toward the inside is provided at the end portion of the endoscope attachment portion 5. An end of the insertion portion 4 of the endoscope 3 is inserted into the endoscope attachment portion 5 from a rear end side thereof, and an end surface of the insertion portion 4 of the endoscope 3 is applied to a rear surface of the endoscope engagement portion 6. As a result, the endoscope 3 is fixed to the mucosa excising device using an endoscope 1 at a position where it does not enter an area of the cap 2. In order to insert and fix the insertion portion 4 of the endoscope in the attachment portion 5, an inside diameter of the attachment portion 5 is substantially the same as an outside diameter of the insertion portion 4, and the insertion portion 4 is inserted into the attachment portion 5 by slightly elastically deforming the attachment portion 5. This enables the insertion portion to be further elastically supported by the attachment portion, which is preferable.

An end surface of the cap 2 defined by an end edge thereof is obliquely formed with respect to an insertion direction of the endoscope 3, i.e., a central axis of the cap 2. Alternatively, the end surface of the cap 2 may be formed vertically to the insertion direction of the endoscope 3.

A claw portion 7 which extends in a circular form along the substantially full circumference and is constituted of a protruding edge portion which protrudes toward the inside is formed at an end peripheral edge of the cap 2. The cap 2 has a base end portion or a base end wall 8 which is continuous to a cylindrical portion. The base end wall 8 is formed into a tapered cylindrical shape or a tapered step from a base end of a cylindrical wall 2a to the endoscope engagement portion 6. A through hole is formed in the base end portion 8 forming the tapered step. An end of a flexible tube 9 having an outside diameter substantially equal to an inside diameter of the through hole is inserted and fixed in this through hole, and a communication opening portion 10 which communicates with the inner side of the cap 2 is defined by an end opening of the flexible tube 9. An end part of the flexible tube 9 extends in an axial direction along an outer peripheral surface of the attachment portion 5, namely, it extends in such a manner that its central axis becomes substantially parallel to a central axis of the attachment portion 5, and the opening at the end is positioned so as to be adjacent to the cylindrical wall of the cap 2. The end part of the flexible tube 9 is fixed to the attachment portion 5 and the cap 2 while maintaining the air-tightness with the endoscope attachment portion 5 by means such as bonding or welding. It is preferable that the flexible tube 9 is formed of a synthetic resin so as to has a flexibility.

Figure 2:
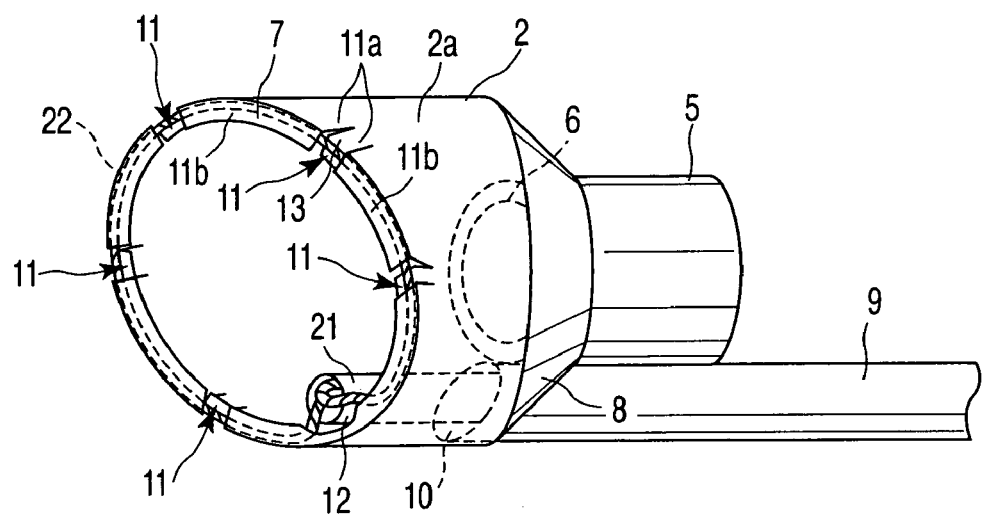
FIG. 2 is a perspective view showing a cap of the mucosa excising device using an endoscope according to the first embodiment.

As shown in FIGS. 2 and 3, the end portion of the flexible tube 9 is positioned on the inner side away from the outer periphery of the cap 2. The flexible tube 9 has a length substantially equal to or larger than an effective length of the insertion portion 4 of the endoscope 3, and it can be positioned over the entire length of the insertion portion.

The claw portion 7 forming the end rim of the cap 2 forms a plurality of engagement portions 11 distanced from each other at equal intervals in the circumferential direction and one snare wire supply portion 12 in cooperation with the end portion of the cylindrical wall 2a of the cap 2 (in the embodiment, the claw portion 7 and the end portion of the cylindrical wall 2a are referred to as a circular end portion of the cap 2). In this embodiment, five engagement portions 11 and one snare wire supply portion 12, i.e., six members in total are arranged at intervals of 60° and constitute a support mechanism which supports an end loop portion of the snare wire 22. The snare wire supply portion 12 is formed at a position corresponding to the communication opening portion 10 formed of the end opening of the flexible tube 9. Each engagement portion 11 has an engagement piece 13 which is a hook-like small piece part by forming at the circular end portion of the cap 2 substantially parallel two notches 11a in a vertical direction or parallel to an axis of the cap 2 with an appropriate gap therebetween so as to extend to the end of the claw portion, the engagement piece 13 being defined between these notches 11a. The circular end portion has the five engagement portions 11 and remaining portions or non-deformed portions (corresponding portions) 11b positioned between the respective adjacent engagement portions 11. Usually, an outer peripheral surface and an inner peripheral surface of the engagement piece 13 of the engagement portion 11 maintains shapes positioned on the same circumferential surface as that of the circular end portion of the cap 2. However, as shown in FIG. 3, when expanding an end portion of the snare wire 22 in a loop form and attaching it along the inner part of the circular end portion, each engagement piece 13 is inclined on the inner side away from the looped end portion of the snare wire 22 with a base end of the engagement piece 13 being used as a swiveling axis, an annular space is defined between each engagement piece 13 and each non-deformed portion 11b of the circular end portion, and the looped end portion of the snare wire 22 is fitted in this space. Thereafter, each engagement piece 13 is returned to its original position, and the looped end portion is pressed against the inner surface of the non-deformed portions 11b by using the outer surfaces of these engagement pieces 13. As a result, the non-deformed portions 11b and the engagement pieces 13 alternately hold the looped end portion of the snare wire 22 in the circumferential direction, and hold it at a fixed position. It is preferable that the swiveling and return to the base of the engagement pieces 13 depend on the elastic deformation of the base end portions of the engagement pieces and the elastic return force.

Figure 1:
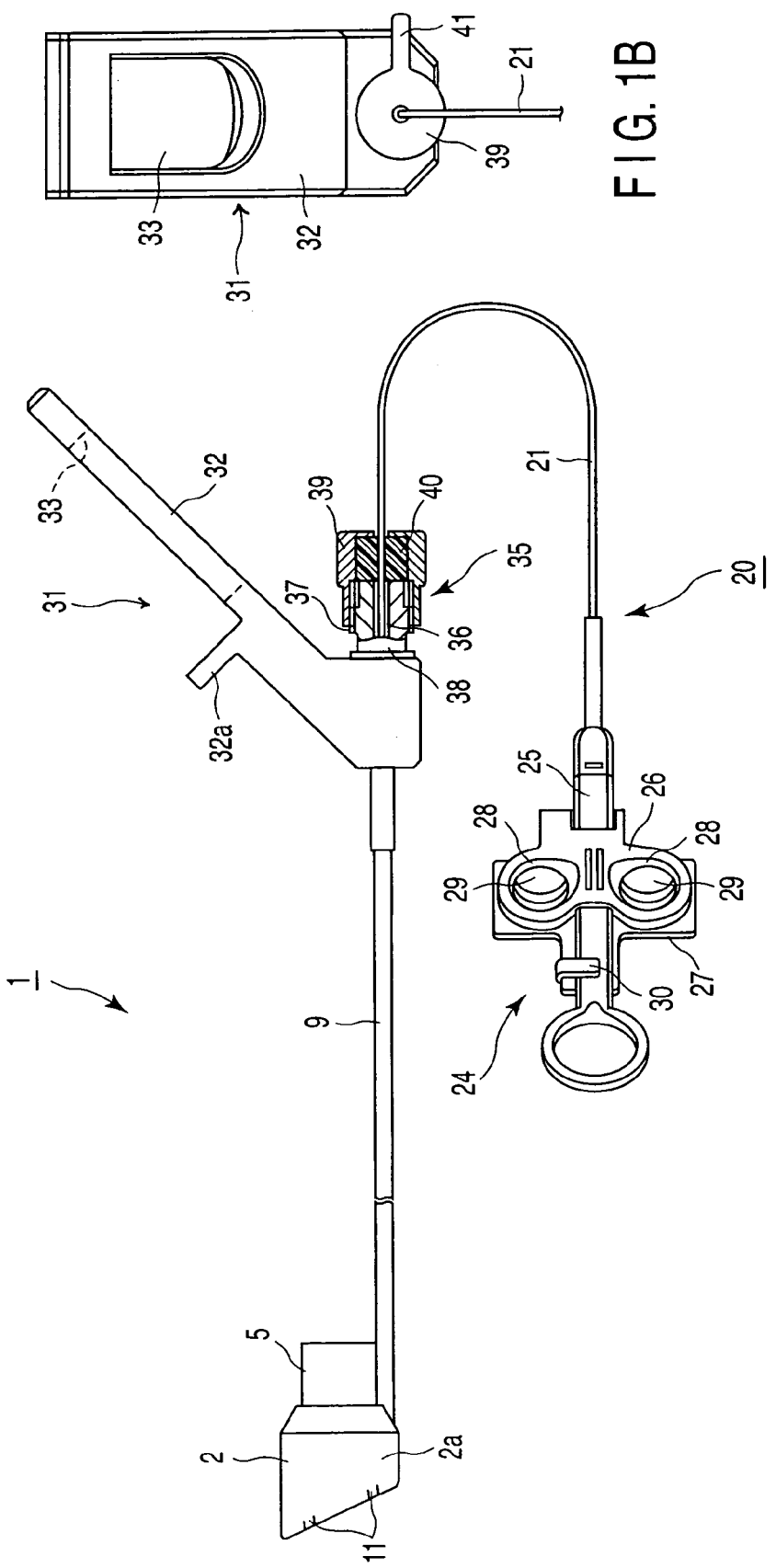
FIG. 1A is a view schematically showing an entire mucosa excising device using an endoscope according to a first embodiment.
FIG. 1B is a front view of a hook which engages a hand side part of a flexible tube of the mucosa excising device using an endoscope depicted in FIG. 1A with an endoscope.

In use, a snare sheath 21 of a high-frequency snare 20 shown in FIG. 1 is inserted into the flexible tube 9, and an end portion of the snare sheath 21 is caused to protrude toward the inside of the cap 2 from the communication opening portion 10 of the cap 2. The snare wire 22 of the high-frequency snare 20 is fed to the snare wire supply portion 12 of the cap 2 from the end of the snare sheath 21, bent in a loop form along the circular end portion of the cap 2, and held at a fixed position by the circular end portion in this state as described above.

As shown in FIG. 1A, the high-frequency snare 20 has an operation portion 24 positioned on a base end portion side of the snare sheath 21. The operation portion 24 has a main body 25 and a slider 26 which is retractably provided on this main body 25. The base end portion of the snare wire 22 is directly connected with the slider 26. To the operation portion 24 is attached a restricting member 27 which appropriately fixes the slider 26 to the main body 25 as means for restricting the part of the snare wire 22 in the cap so as not to move. The restricting member 27 is detachable with respect to the operation portion 24, and includes convex portions which are respectively tightly inserted into a pair of fingerhold hole portions 28 of the slider 26, and a fixing portion 30 which fixes the restricting member 27 to the main body 25 of the operation portion 24.

As shown in FIG. 1A, on the operator's hand side of the flexible tube 9 forming the tube main body are provided a hook 31 which engages with a base end portion of the endoscope and fixing means 35 which can fix the snare sheath 21 of the high-frequency snare 20 so as to be capable of being released. The fixing means 35 has a cylindrical base portion 38 in which a through hole 36 communicating with the inside of the flexible tube 9 is formed along the central axis, and which has a screw portion or a male screw 37 formed on an outer peripheral surface thereof. A turning ring 39 having a screw portion or a female screw formed on an inner surface thereof is engaged with the screw portion 37. The inside of this turning ring 39 has a cylindrical shape that a base end is closed, and a cylindrical elastic tube 40 is air-tightly accommodated in the turning ring 39 in a state that end surfaces of the tube 40 are respectively in contact with the inner surface of the base end and the base end surface of the base portion 38. The snare sheath 21 inserted through a hole formed in a base end wall of the turning ring 39 pierces through a central hole of the elastic tube 40. The snare sheath 21 is further inserted into the flexible tube 9 via the through hole 36 of the base portion 38, As shown in FIG. 1B, a knob (lever) 41 which laterally extends is provided to the turning ring 39. When the turning ring 39 is operated to rotate by the knob 41, the turning ring 39 moves in an axial direction with respect to the base portion 38, and the inner elastic tube 40 can be tightened or released between the turning ring 39 and the base portion 38. When the turning ring 39 is moved in the direction of the base portion 38, the inner elastic tube 40 is compressed and pressure-welded to the part of the snare sheath 21 inserted in this central hole, thereby fixing the snare sheath 21. When the turning ring 39 is moved in the opposite direction and released, the squashed elastic tube 40 is restored, the fixed snare sheath 21 is released, and the snare sheath 21 can move forward and backward.

Figures 4A, 4B, 4C:
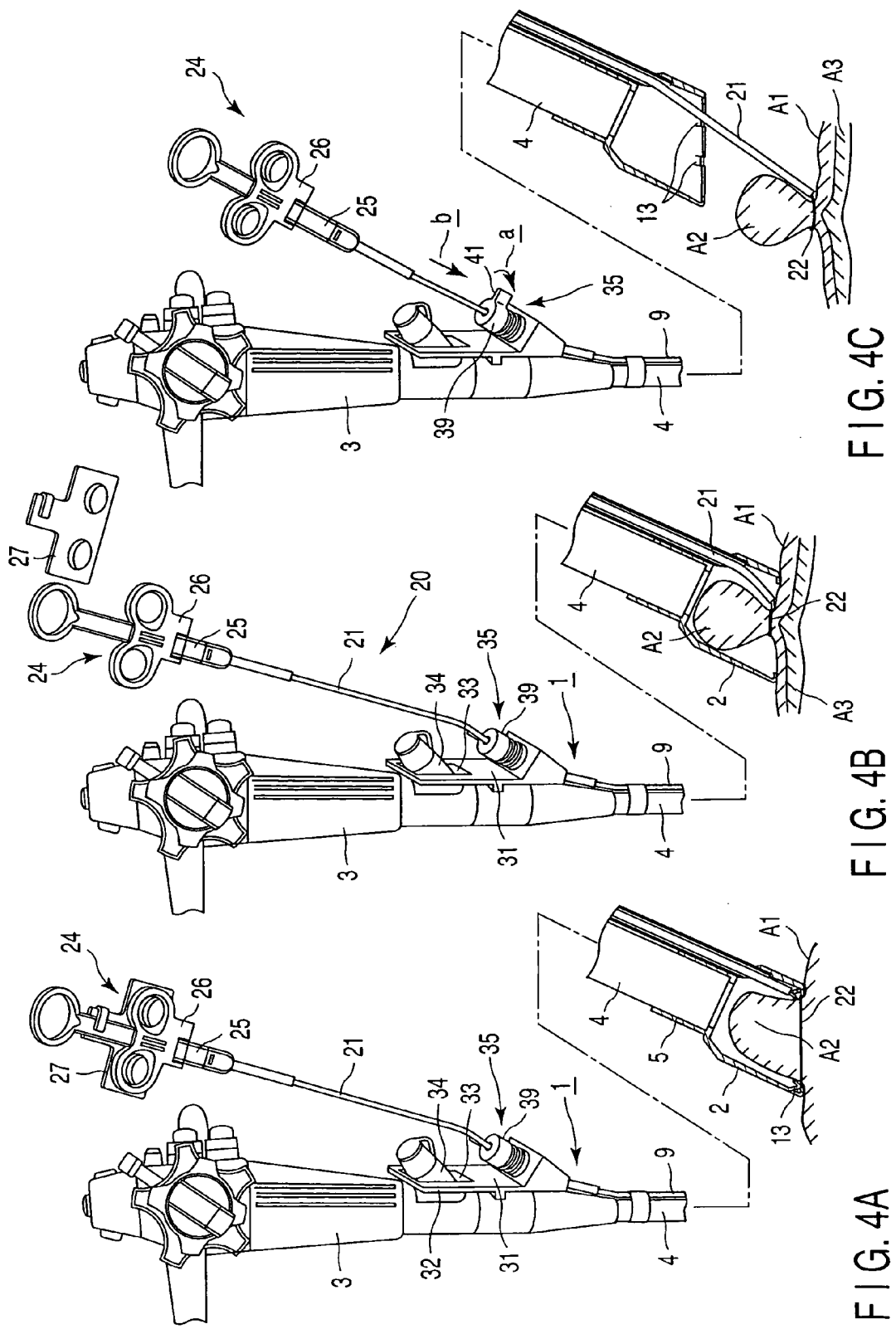
FIGS. 4A to 4C are views illustrating an operation utilizing the mucosa excising device using an endoscope according to the first embodiment.
Figure 5:
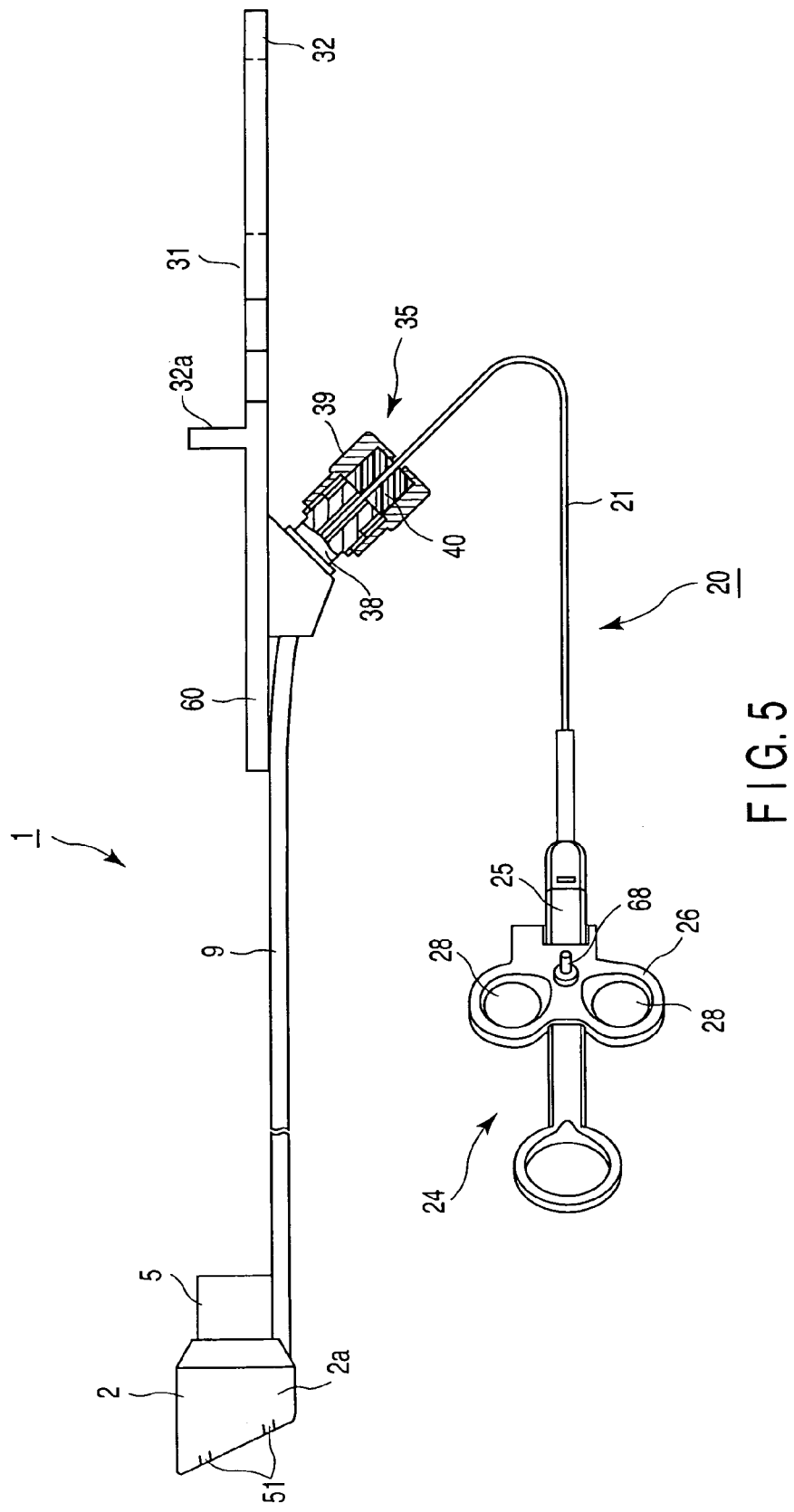
FIG. 5 is a partially cutaway side view showing an entire mucosa excising device using an endoscope according to a second embodiment.

The hook 31 has a hook portion (engagement portion) 32 which engages with the base end portion of the endoscope 3. In the hook portion 32 is formed an engagement hole 33 or a communication opening into which the base end portion of the endoscope 3, e.g., a part of the operation main body is caught (specifically, the hook portion 32 includes a main body which is provided at the base end portion of the flexible tube 9 and engages with the base end portion of the endoscope, and an engagement hole 33 formed in the main body). In this embodiment, as shown in FIG. 4A, a mouth ring portion 34 of a forceps stopper is inserted into and engaged with the engagement hole 33. On the hook portion 32 is provided a leg portion 32a which is used for positioning of the hook 31 at the base end portion of the endoscope 3 when attached in the endoscope 3.

A description will now be given as to a case that a mucosa A1 in a body cavity is excised by utilizing the mucosa excising device 1 using an endoscope. First, the cap 2 of the mucosa excising device using an endoscope 1 is attached at the end of the insertion portion 4 of the endoscope 3, the flexible tube 9 is arranged parallel to the insertion portion 4 of the endoscope 3 (arranged on the outer surface of the insertion portion 4 along its axial direction), and it is fixed to the insertion portion 4 by using a medical tape or the like. Further, the hook 31 is caught on and fixed to the mouth ring portion 34 of the forceps stopper of the endoscope 3. In this fixed state (state that the hook portion 32 is engaged with the mouth ring portion 34 of the forceps stopper), as shown in FIG. 4A, the base end side opening of the flexible tube 9 (opening of the through hole 36 (FIG. 1A) of the fixing means 35) is positioned in the vicinity of the opening of the mouth ring portion 34 of the forceps stopper, and it is also positioned away from the opening of the mouth ring portion 24 in the axial direction of the operation portion (base end portion) of the endoscope 3. In this state, the base end side opening of the flexible tube 9 (opening of the through hole 36 of the fixing means 35) and the opening of the mouth ring portion 34 of the forceps stopper are positioned in substantially the same plane, and directed in substantially the same direction. If the base end side opening of the flexible tube 9 and the opening of the mouth ring portion 34 of the forceps stopper form such an arrangement relationship, these openings are directed in the same direction in close proximity to each other on the same side (in the same plane), and the openings are fixed with respect to the endoscope. Therefore, insertion of the treatment instrument into these openings can be facilitated. The restricting member 27 is attached to the operation portion 24 of the high-frequency snare 20 in such a manner that the slider 26 does not move relative to the main body 25.

In this state, as shown in FIG. 4A, the endoscope 3 and the mucosa excising device using an endoscope 1 are inserted into a body cavity, the end opening portion of the cap 2 of the mucosa excising device using an endoscope 1 is moved toward a target mucosa excision part A2 of the mucosa A1 in the body cavity, and the opening portion of the end portion of the cap 2 is pressed against the mucosa A1. In this state, when the inside of the cap 2 is exhausted by using a non-illustrated suction device through the channel of the endoscope 3, the mucosa A1 is sucked into the cap 2 by its negative pressure, and the excision part A2 of the mucosa A1 is raised.

Subsequently, as shown in FIG. 4B, the restricting member 27 is removed from the operation portion 24 of the high-frequency snare 20, and the slider 26 of the operation portion 24 is retired with respect to the main body 25. As a result, the snare wire 22 is pulled into the snare sheath 21, and the loop part engaged by the respective engagement portions 11 is also pulled, thereby deforming the engagement portions 11. Consequently, the loop part comes off the engagement portions 11 and is positioned around the excision part A2 of the mucosa A1. When the loop part is further pulled, the root of the excision part A2 of the mucosa A1 is tightly bound.

Then, as shown in FIG. 4C, when the turning ring 39 is rotated in a direction indicated by an arrow a by using the knob 41 of the fixing means 35, fixation of the fixing means 35 is loosened, and fixation of the snare sheath 21 of the high-frequency snare 20 is released. In this state, the snare sheath 21 is moved in a direction indicated by an arrow b and pushed into the flexible tube 9. Then, the insertion portion 4 of the endoscope 3 is pulled in such a manner that the end part of the snare sheath 21 protrudes from the end opening of the cap 2, and the cap is retracted from the mucosa A1. As a result, the excision part A2 tightly bound by the snare wire 22 moves out of the cap 2, and it is positioned in front of the cap 2. In this state, a state of the mucosa A1 or a muscular coat A3 is checked by using an ultrasonic probe or the like inserted into the channel of the endoscope 3. When a state that the muscular coat A3 is not caught in the excision part A2 is confirmed as a result of this check, it is determined that safe excision of the mucosa A1 is possible. In a state shown in FIG. 4C, a high-frequency current is passed to the snare wire 22 while tightening the excision part A2 by using the looped part of the snare wire 22, and the excision part A2 is cut off from the mucosa A1.

Then, after the ultrasonic probe or the like is removed from the channel, the inside of the cap 2 is exhausted through the channel of the endoscope 3, and the excision part A2 is sucked and taken into the cap 2. Subsequently, with the excision part A2 being held in the cap 2, it is taken to the outside of the body cavity together with the endoscope 3, and collected.

In the mucosa excising device using an endoscope 1 according to this embodiment, the snare wire 22 of the high-frequency snare 20 can be previously arranged and held in a loop form at a predetermined position in the cap 2 by an operation performed outside a body cavity before this mucosa excising device is used for the endoscopic mucosal resection. The snare wire 22 fed from the inside of the snare sheath 21 of the high-frequency snare 20 is expanded in a loop form and arranged along the circular end portion of the cap 2, and it is alternately supported between the engagement pieces 13 and the non-deformed portions 11b while being pressed against the inner surfaces of the non-deformed portions 11b by the outer surfaces of the engagement pieces 13. Therefore, the snare wire 22 can be attached at a predetermined position in the cap 2 so as not to come off. At the same time, since the snare sheath 21 of the high-frequency snare 20 inserted into the flexible tube 9 is fixed by using the fixing means 35 and the snare sheath 21 is prevented from accidentally moving, the snare sheath 21 does not accidentally move, and the snare wire does not come off the predetermined attachment position in the cap 2. Moreover, even if the cap 2 is deformed during insertion into a body cavity or a treatment in the body cavity, the loop of the snare wire 22 can be prevented from coming off the attachment position in the cap 2.

From the above-described series of explanation, it can be understood that there are a first technique that the part of the snare wire 22 arranged in the loop form at the predetermined position in the cap 2 is assuredly held between the engagement pieces 13 and the non-deformed portions 11b at the circular end portion of the cap 2 and a second technique that the fixing means 35 for fixing the snare sheath 21 of the high-frequency snare 20 inserted into the flexible tube 9 is combined with the above-described matter.

Here, in the second technique that the snare sheath 21 of the high-frequency snare 20 inserted into the flexible tube 9 and led into the cap 2 is fixed by the fixing means 35 and the snare sheath 21 is prevented from accidentally moving, it is possible to avoid the accidental movement of the snare wire 22 due to the movement of the snare sheath 21 with respect to the flexible tube 9. For example, when the snare wire 22 is arranged in the loop form at the predetermined position in the cap 2, there is demonstrated an original advantage that the attachment position of the snare wire 22 arranged in the loop form can be stably maintained. Therefore, the snare wire 22 can be arranged in the loop form with respect to the cap 2 without using holding means such as the circular end portion having the claw portion 7. In such a case, there is also demonstrated an advantage that the snare wire loop does not accidentally come off the cap during insertion into a body cavity or at treatment in the body cavity when conducting the endoscopic mucosal resection.

In this embodiment, since the mucosa excising device using an endoscope 1 can be inserted into a body cavity with the snare wire 22 being attached in the loop form in the cap 2 when conducting the endoscopic mucosal resection, it is not necessary to perform looping of the snare wire 22 after inserting the mucosa excising device using an endoscope 1 into a body cavity.

Second Embodiment

A mucosa excising device using an endoscope according to a second embodiment of the present invention will now be described with reference to FIGS. 5 to 9.

Figures 7A, 7B:
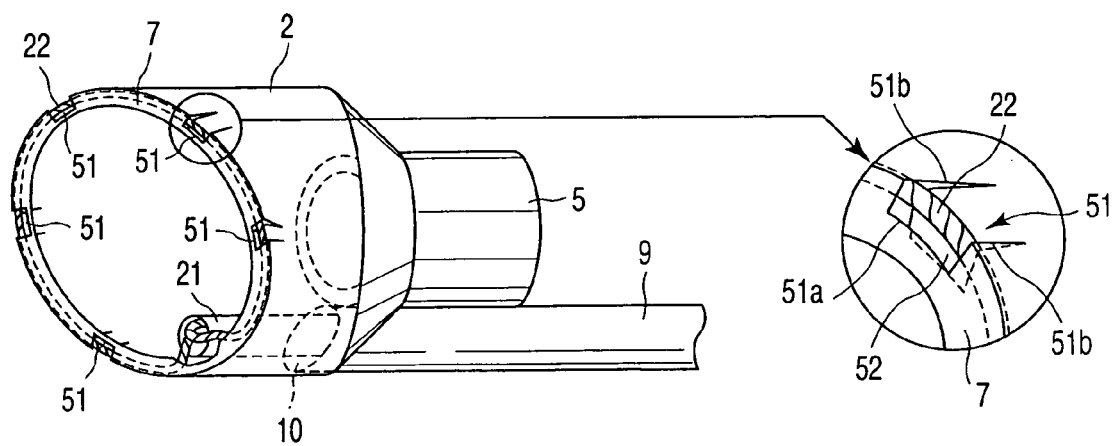
FIG. 7A is a perspective view showing a cap of the mucosa excising device using an endoscope according to the second embodiment.
FIG. 7B is an enlarged cross-sectional view showing a part surrounded by a circle in FIG. 7A.

In this mucosa excising device using an endoscope 1 according to this embodiment, a structure of each engagement portion 51 at the circular end portion of the cap 2 is different from that in the first embodiment. In this embodiment, as shown in FIGS. 7A and 7B, an engagement piece 52 of each engagement portion 51 is formed by forming a lateral notch 51a at a substantially central portion of the claw portion 7 and two vertical notches 51b from both ends of the notch 51a to the wall 2a of the cap 2. That is, the parallel notches 51b do not extend to the end of the claw portion 7 like the notches 11a in the foregoing embodiment. As shown in FIGS. 8A and 8B, each engagement piece 52 defined by the three notches 51a and 51b is inclined to the inner side with respect to each remaining part or non-deformed portion 52a at the circular end portion positioned between the engagement pieces 52, and an outer surface of each engagement piece 52 presses the snare wire 22 against an inner surface of each non-deformed portion 52a. The snare wire 22 is thereby held and supported alternately by the non-deformed portions 52a and the engagement pieces 52.

Since the notches are eliminated from the end edge portion of the claw 7 by forming each engagement piece 52 in such a shape, namely, the ends of the claw portion 7 are continuous and connected with each other, the strength of the end edge of the cap 2 is increased, and the cap 2 itself is hardly deformed. Additionally, the end edge portion which protrudes to the inner side of the claw portion 7 becomes smooth.

Figure 6:
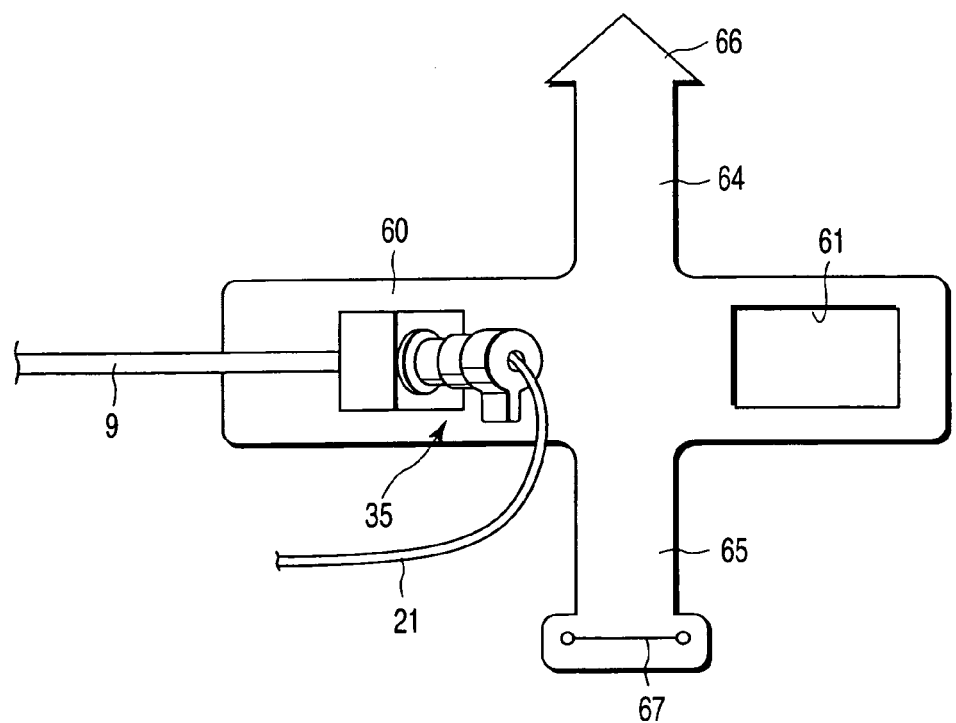
FIG. 6 is a developed view of a hook of the mucosa excising device using an endoscope depicted in FIG. 5.

Further, in this embodiment, a structure of fixing means 35 provided on an operator's hand side of the flexible tube 9 is different from that in the first embodiment. This fixing means 35 is fixed on one surface of a sheet (main body) 60 having such a shape as shown in FIG. 6. The sheet 60 has an engagement hole 61 which engages with a mouth ring portion 34 of a forceps stopper of, e.g., an operation main body 62 (shown in FIG. 9) at the base end portion of the endoscope 3, and bands 64 and 65 extending to the side so as to be capable of fixing when wound around the operation main body 62 of the endoscope 3. An insertion portion 66 is provided at an end of one band 64, and an insertion opening 67 is formed in the vicinity of an end of the other band 65. When the insertion portion 66 is inserted into the insertion opening 67 as shown in FIG. 9, the bands 64 and 65 are wound around the operation main body 62 of the endoscope 3, and the base end portion of the mucosa excising device using an endoscope 1 can be firmly fixed to the endoscope 3.

Furthermore, in this embodiment, in regard to the operation portion 24 of the high-frequency snare 20, the movement of the slider 26 relative to the main body 25 of the operation portion 24 is restricted in the following structure. A through hole is formed in the slider 26, and a bore aligned with respect to this through hole is formed to the main body 25 at a fixing position of the slider 26. At the fixing position, a pin 68 as a restricting member is inserted into the bore of the main body 25 via the through hole of the slider 26. Therefore, the movement of the slider 26 relative to the main body 25 is obstructed by this pin 68, and the both members are fixed. Further, when the pin 68 is removed from the both members, the slider 26 can move with respect to the main body 25.

The structures other than the above are the same as those in the first embodiment. Furthermore, in regard to the effect of this embodiment, a method of fixing the base end portion of the mucosa excising device using an endoscope 1 to the endoscope 3 and a method of canceling the restriction of the slider 26 are different from those in the first embodiment. That is, when fixing the base end of the mucosa excising device using an endoscope 1 to the endoscope 3, the main body is caught in the vicinity of the mouth ring portion 34 of the forceps stopper of the endoscope 3, the bands 64 and 65 are then wound around the operation main body 62 of the endoscope 3, and the insertion portion 66 is inserted into and fixed to the insertion opening 67.

Moreover, when canceling the restriction of the slider 26, the pin 68 is removed from the slider 26.

As the advantages of this embodiment, besides the advantages of the first embodiment, there is an advantage that the mucosa excising device using an endoscope 1 can be firmly fixed to the endoscope 3.

Third Embodiment

A mucosa excising device using an endoscope according to a third embodiment of the present invention will now be described with reference to FIGS. 10A to 11. The mucosa excising device using an endoscope 1 according to this embodiment uses engagement pieces 52 of engagement portions 51 formed at the circular end portion of the cap 2 having the same structure as that of the second embodiment, and a guide groove 71 into which the snare wire 22 is inserted is formed on an outer surface of each engagement piece 52 in a direction along which the snare wire 22 extends. When the snare wire 22 is held between the engagement pieces 52 and the non-deformed portions formed at the circular end portion of the cap 2, it is fitted in the guide grooves 71 formed to the engagement pieces, and hence the snare wire 22 is firmly positioned and fixed at the attachment position.

Any other structures are the same as those in the second embodiment mentioned above. Additionally, this embodiment demonstrates the same effects/advantages as those in the above-described second embodiment.

Fourth Embodiment

A mucosa excising device using an endoscope 1 according to a fourth embodiment of the present invention will now be described with reference to FIGS. 12A and 12B.

The mucosa excising device using an endoscope 1 according to this embodiment has engagement portions formed at the circular end portion of the cap 2 different from those of the other embodiments. As shown in FIG. 12B, an engagement piece 77 of each engagement portion 75 is defined by a notch 76a formed at the end edge of the cylindrical wall 2a of the cap 2 so as to extend in the lateral direction, and two vertical notches 76b formed at the wall 2a parallel to the axis so as to extend rearward from both ends of the notch 76a. The lateral notch 76a is formed so as to obliquely extend to a boundary between the wall 2a and the claw portion 7 as shown in FIG. 12A. As a result, although each engagement piece 77 is tabular, a small protrusion is formed at the end thereof.

The engagement pieces 77 are inclined to the inner side from the circular end portion, outer surfaces of the engagement pieces 77 press the snare wire 22 by pushing it against the non-deformed portions 77a, and the engagement pieces 77 and the claw portion 7 alternately support the snare wire 22. Since the part of the claw portion 7 remains in its integrity by forming each engagement piece 77 into such a tabular shape, the strength of the end edge of the cap 2 is increased, and the cap 2 is hardly deformed. Other effects/advantages of this embodiment are the same as those of the foregoing embodiments.

Fifth Embodiment

A mucosa excising device using an endoscope according to a fifth embodiment of the present invention will now be described with reference to FIGS. 13 to 15B.

The mucosa excising device using an endoscope 1 according to this embodiment has each engagement portion 81 formed at the circular end portion of the cap 2 different from those in the other embodiments. As shown in FIG. 14, the engagement portion 81 in this example is constituted of a lateral notch 82a formed at the end edge of the cap 2 so as to avoid the claw portion 7, and an engagement piece 83 sectioned and formed by forming two vertical notches 82b parallel to each other from both ends of the notch 82a to the peripheral wall 2a of the cap 2. Such a structure is the same as that of the engagement portion according to the fourth embodiment. In this embodiment, a protrusion 84 is provided on the outer peripheral surface at the end portion of the wall 2a between the two vertical notches 82b.

Each engagement piece 83 of the engagement portion 81 is inwardly inclined from a state shown in FIG. 15A to a state depicted in FIG. 15B, the snare wire 22 is pressed by using an outer surface and the protrusion 84 of each engagement piece 83, and the claw portion 7 and the engagement pieces 83 alternately support the snare wire 22. According to this structure, the engagement piece 83 of the engagement portion 81 has the protrusion 84, and the protrusion 84 engages with the snare wire 22 and acts as an engagement protrusion which prevents the snare wire 22 from coming off the engagement portion 81. Therefore, the snare wire 22 can be further firmly engaged with each engagement portion 81. Furthermore, other effects/advantages of this embodiment are the same as those of the foregoing embodiments.

Sixth Embodiment

A mucosa excising device using an endoscope according to a sixth embodiment of the present invention will now be described with reference to FIGS. 16A and 17.

To the mucosa excising device using an endoscope 1 according to this embodiment are provided notch portions 80 obtained by notching an area of the claw portion 7 to the end. On the inner side of each notch portion 80, a flange 82 which is slightly inclined in the direction of the claw portion 7 with a distance substantially corresponding to a thickness of the snare wire 22 from the claw portion 7 is provided so as to protrude from the inner surface of the cylindrical wall 2a. In this manner, each engagement portion 81 is formed of the flange 82 and the remaining part of the claw portion 7. The flange 82 may be formed of the part of the claw portion 7 cut and raised when notching the notch portion 80.

A fed portion or a loop portion 12 of the snare wire is arranged between the claw portion 7 and the flange 82 of each engagement portion 81, and held and maintained therebetween. It is preferable that the claw portion 7 and the flange 8 are elastically deformed and hold the fed portion 12 of the snare wire. In order to realize this, it is preferable that a distance between the claw portion 7 and the flange 82 is slightly shorter than a diameter of the loop portion 12.

Any other structures are the same as those of the first embodiment mentioned above. Moreover, the effects/advantages of this embodiment are the same as those of the above-described first embodiment.

Seventh Embodiment

A mucosa excising device using an endoscope according to a seventh embodiment of the present invention will now be described with reference to FIGS. 18.

In the mucosa excising device using an endoscope 2 according to this embodiment, an adhesive with a weak adhesive power is applied on the flange 82 of the above-described sixth embodiment, and the snare wire 22 is bonded and fixed to the flange portion 82. As a result, even if a distance between the claw portion 7 and the flange 82 is longer than a diameter of the loop portion of the snare wire, the snare wire 22 can be fixed. Additionally, if this distance is short, fixation of the snare wire 2 becomes more secure. Since the adhesive 85 used in this example has a weak adhesive power, there is no trouble in a handling operation itself of the snare wire 22. Any other structures are the same as those of the sixth embodiment. Further, the effects/advantages of this embodiment are the same as those of the first embodiment mentioned above.

The present invention is not restricted to each of the foregoing embodiments, and various modifications should be allowed. The engagement piece in the engagement portion according to the present invention is not restricted to the conformation that the engagement portion is provided at least to the part of the cap in the vicinity of the end edge thereof and this engagement portion presses the snare wire from the inner side with respect to the protrusion portion of the cap, and a conformation that the snare wire is pressed from the outer side may be adopted.

Figure 19:
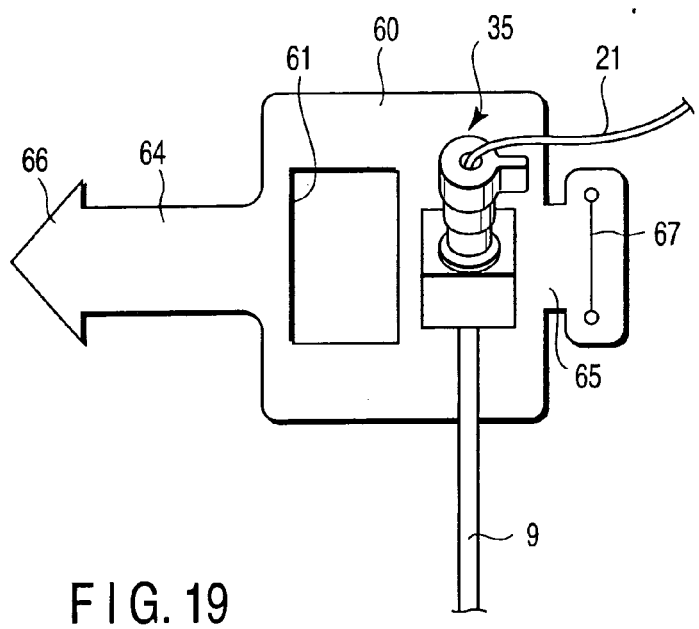
FIG. 19 is a plane view showing a first modification of a hook portion (engagement portion) provided on a base end side of a flexible tube.
Figure 20:
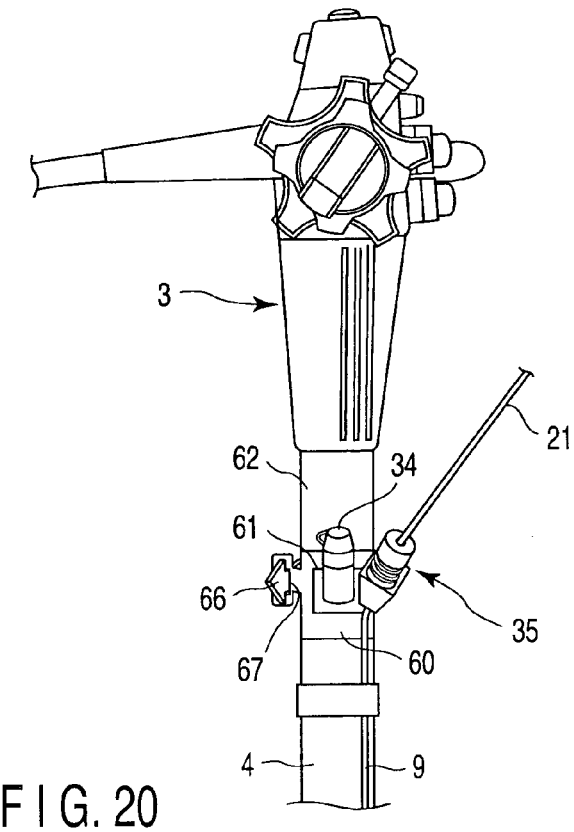
FIG. 20 is a perspective view showing a state that the hook portion according to the first modification is attached.

Furthermore, the conformation of the hook portion (engagement portion) provided on the base end side of the flexible tube 9 is not restricted that in the foregoing embodiment, and a structure of each modification described below may be used. FIGS. 19 and 20 show a first modification of the second embodiment. Therefore, like reference numerals denote the same constituent elements as those in the second embodiment (FIG. 6). In this modification, as shown in FIG. 19, an engagement hole 61 which engages with the mouth ring portion 34 of the forceps stopper and fixing means 35 of the flexible tube 9 are provided so as to be aligned alongside on the sheet 60. Bands 64 and 65 which are wound around the operation portion main body 62 (shown in FIG. 20) of the endoscope 3 and fix it are provided on both sides of the sheet 60 so as to extend to the sides.

As shown in FIG. 20, with the engagement hole 61 engaging with the mouth ring portion 34 of the forceps stopper, the base end side opening of the flexible tube 9 is arranged so as to be positioned away from (substantially adjacent to) the opening of the mouth ring portion 34 of the forceps stopper in the circumferential direction of the operation portion (base end portion) of the endoscope 3.

FIG. 21 shows a second modification of the second embodiment. Therefore, like reference numerals denote the same constituent elements as those in the second embodiment (FIG. 6). In this modification, an engagement slit 64a is formed along the longitudinal direction of one band 64. This engagement slit 64a is engaged with a flange-shaped portion 100 at an end portion of the other band 65. For example, the engagement slit 64a is elastically expanded, and the flange-shaped portion 100 is elastically engaged in the engagement slit 64a. As a result, the bands 64 and 65 can surround the operation main portion 62 of the endoscope 3 and can be fixed thereto.

FIG. 22 shows a third modification of the second embodiment. Therefore, like reference numerals denote the same constituent elements as those in the second embodiment (FIG. 2). In this modification, the bands 64 and 65 are not provided, but a rear surface of the sheet 60 is an adhesive face. For example, an adhesive sheet is attached to the rear surface of the sheet 60, or the sheet 60 is formed of a magic tape. That is, in this modification, the engagement portion has an adhesive face which can be detachably disposed on the surface of the operation portion of the endoscope 3 by a predetermined adhesive power.

FIG. 23 shows a fourth modification of the second embodiment. Therefore, like reference numerals denote the same constituent elements as those in the second embodiment (FIG. 6). In this modification, an engagement hole 61 has a circular shape corresponding to a shape of the mouth ring portion 34 of the forceps stopper. A notch 102 is formed to the sheet 60 from this engagement hole 61 toward the end edge of the sheet 60. The notch 102 has a width smaller than a diameter of the engagement hole 61 and can be elastically expanded. A tapered portion 102a which can smoothly guide the mouth ring portion 34 of the forceps stopper into the engagement hole 61 through the notch 102 is formed at the end portion of the notch 102. According to such a structure, the engagement hole 61 (engagement portion) can be engaged with the mouth ring portion 34 of the forceps stopper by using an elastic force.

According to the above description, it is possible to obtain the following matters, matters acquired by appropriately combining these matters, and combinations of these matters and various conformations.

As the conformations according to the present invention, the following mucosa excising device using an endoscope can be preferably provided.

1. A mucosa excising device using an endoscope comprising:

a transparent cap which has a substantially cylindrical shape and a protrusion portion which protrudes in a flange form provided on an inner side of an inner peripheral surface in the vicinity of an end edge thereof;

a fixing portion which fixes the cap to an end portion of the endoscope;

a flexible tube whose opening on an end side communicates with the inner side of the cap, and which is aligned outside an insertion portion of the endoscope when the cap is fixed to the endoscope; and a high-frequency snare inserted into the flexible tube, and a snare wire being expanded and arranged along the inner peripheral surface of the cap, wherein at least one engagement portion having an engagement piece formed by notching a part of the cap in the vicinity of the end edge thereof is provided, and the snare wire is supported and arranged alternately by the engagement portion and the protrusion portion and fixed to the cap.

2. A mucosa excising device using an endoscope comprising: a transparent cap which has a substantially cylindrical shape and a protrusion portion which protrudes in a flange form provided on an inner side of an inner peripheral surface in the vicinity of an end edge thereof; a fixing portion which fixes this cap to an end portion of the endoscope; a flexible tube whose opening on an end side communicates with the inner side of the cap, and which is aligned outside an insertion portion of the endoscope when the cap is fixed to the endoscope; and a high-frequency snare inserted into the flexible tube, a snare wire being expanded and arranged along the inner peripheral surface of the cap, wherein fixing means for fixing a sheath of the high-frequency snare so as to be capable of being released is provided at a base end portion of the flexible tube.

3. A mucosa excising device using an endoscope according to the additional statement 1 or 2, wherein the snare wire is fixed to the engagement portion by using an adhesive member.

4. A mucosa excising device using an endoscope according to the additional statement 1 2, wherein the high-frequency snare has a handle including a slider which moves back and forth the snare wire, and a restricting member which restricts the forward and backward movement of the slider is detachably provided on the handle.

5. A mucosa excising device using an endoscope according to the additional statement 1 2, wherein an engaging portion which engages with the snare wire is provided on the engagement portion.

6. A mucosa excising device using an endoscope according to the additional statement 5, wherein the engaging portion is a concave portion formed on an outer surface of the engagement portion.

7. A mucosa excising device using an endoscope according to the additional statement 5, wherein the engaging portion is a protrusion portion formed on an outer surface of a wall of the cap.

8. An endoscopic external channel tube comprising: a tube main body arranged on an outer surface of an insertion portion of an endoscope along its axial direction; and an engagement portion which is provided at a base end portion of the tube main body and to a base end side operation portion of the endoscope and can be engaged with a mouth ring portion of a forceps stopper.

9. An endoscopic external channel tube according to the additional statement 8, wherein the base end side opening of the tube main body is positioned in the vicinity of an opening of the mouth ring portion of the forceps stopper in a state that the engagement portion is engaged with the mouth ring portion of the forceps stopper.

10. An endoscopic external channel tube according to the additional statement 8 or 9, wherein the base end side opening of the tube main body is formed so as to be positioned away from the opening of the mouth ring potion of the forceps stopper in an axial direction of the operation portion of the endoscope in a state that the engagement portion is engaged with the mouth ring portion of the forceps stopper.

11. An endoscopic external channel tube according to any of the additional statements 8 to 10, wherein the base end side opening of the tube main body and the opening of the mouth ring portion of the forceps stopper are formed so as to be positioned in substantially the same plane in a state that the engagement portion is engaged with the mouth ring portion of the forceps stopper.

12. An endoscopic external channel tube according to any of the additional statements 8 to 11, wherein the base end side opening of the tube main body and the opening of the mouth ring portion of the forceps stopper are formed so as to be directed in substantially the same direction in a state that the engagement portion is engaged with the mouth ring portion of the forceps stopper.

13. An endoscopic external channel tube according to the additional statements 8 or 9, wherein the base end side opening of the tube main body is formed so as to be positioned being substantially adjacent to (or distanced from) the mouth ring portion of the forceps stopper (or the opening of the mouth ring portion) in a circumferential direction of an operation portion of the endoscope in a state that the engagement portion is engaged with the mouth ring portion of the forceps stopper.

14. An endoscopic external channel tube according to any of the additional statements 8 to 13, wherein the engagement portion includes a main body which is provided at the base end portion of the tube main body and engages with the base end portion of the endoscope, and an engagement hole which is formed in the main body and caught on the mouth ring portion of the forceps stopper.

15. An endoscopic external channel tube according to any of the additional statements 8 to 13, wherein the engagement portion is engaged with the mouth ring portion of the forceps stopper by its elastic force.

16. An endoscopic external channel tube according to any of the additional statements 8 to 14, wherein the engagement portion has bands wound around and fixed to the operation portion of the endoscope.

17. An endoscopic external channel tube according to any of the additional statements 8 to 14, wherein the engagement portion has an adhesive face which is detachably disposed on a surface of the operation portion of the endoscope by a predetermined adhesive power.

18. An endoscopic external channel tube comprising: a tube main body which is arranged on an outer surface of an insertion portion of an endoscope along its axial direction; and an engagement portion which is provided at a base end portion of the tube main body and can engage with a base end portion of the endoscope.

19. An endoscopic external channel tube comprising: a tube main body which is arranged on an outer surface of an insertion portion of an endoscope along its axial direction; and an engagement portion which is provided at a base end portion of the tube main body and can engage with a base end portion of the endoscope, wherein a base end side opening of the tube main body is formed so as to be positioned in the vicinity of an opening of a mouth ring portion of a forceps stopper provided on a base end side operation portion of the endoscope in a state that the engagement portion is engaged with the base end side operation portion of the endoscope.

20. An endoscopic external channel tube comprising: a tube main body which is arranged on an outer surface of an insertion portion of an endoscope along its axial direction; and an engagement portion which is provided at a base end portion of the tube main body and can engage with a base end portion of the endoscope, wherein the base end side opening of the tube main body and the opening of the mouth ring portion of the forceps stopper provided on the base end side operation portion of the endoscope are formed so as to be directed in substantially the same direction in a state that the engagement portion is engaged with the base end side operation portion of the endoscope.

21. An endoscopic external channel tube comprising: a tube main body which is arranged on an outer surface of an insertion portion of an endoscope along its axial direction; and an engagement portion which is provided at a base end portion of the tube main body and can engage with a base end portion of the endoscope, wherein the base end side opening of the tube main body and the opening of the mouth ring portion of the forceps stopper provided on the base end side operation portion of the endoscope are formed so as to be positioned in substantially the same plane in a state that the engagement portion is engaged with the base end side operation portion of the endoscope.

22. An endoscopic external channel tube comprising: a tube main body which is arranged on an outer surface of an insertion portion of an endoscope along its axial direction; and an engagement portion which is provided at a base end portion of the tube main body and can engage with a base end portion of the endoscope, wherein the base end side opening of the tube main body is formed so as to be positioned being distanced from the opening of the mouth ring portion of the forceps stopper provided on the base end side operation portion of the endoscope in the axial direction of the operation portion of the endoscope in a state that the engagement portion is engaged with the base end side operation portion of the endoscope.

23. An endoscopic external channel tube according to any of the additional statements 8 to 22, wherein a cap (cap 2 disposed at an end of the endoscope) is arranged at an end of the tube main body.

(Objects/Advantages of Each Additional Statement)

An object of the additional statement 1 is securely fixing the loop of the snare wire so as not to readily come off the cap, and its advantage lies in that the loop of the snare wire does not come off the cap even if the cap is deformed at the time of insertion into a body cavity or during a treatment in the body cavity.

An object of the additional statement 2 is preventing the loop from moving by fixing the sheath of the high-frequency snare on the operator's hand side, and its advantage lies in that the loop of the snare wire does not easily come off the cap.

An object of the additional statement 3 is further securely fixing the loop of the snare wire to the cap, and its advantage lies in that the loop does not easily come off the cap.

An object of the additional statement 4 is preventing the loop of the snare wire from moving from a predetermined support position by fixing the slider of the handle of the high-frequency snare on the operator's hand side. Further, its advantage lies in that the loop of the snare wire does not easily come off the cap.

An object of the additional statements 5, 6 and 7 is further securely fixing the snare wire (loop) to the cap, and their advantage lies in that the snare wire (loop) does not easily come off the cap.

The endoscopic external channel tube according to the additional statements 8 to 23 does not assume that the cap is provided at the end, and it is proposed as the endoscopic external channel tube which is independent from the mucosa excising device using an endoscope 1 having the high-frequency snare 20 according to the foregoing embodiments. Conventionally, a base end side opening of an external sheath (endoscopic external channel tube) faces a direction different from a forceps opening 34 (e.g., an opposite side), and there is a problem in that a treatment device is hard to be inserted into the forceps opening 34 or the like. Furthermore, since the base end side opening of the external sheath is not fixed in the conventional example, a treatment device is hard to be inserted into the forceps opening 34 or the like. Conversely, in the endoscopic external channel tube according to the additional statements 8 to 23, its base end side opening is directed in the same direction on the same side (in the same plane) as the forceps opening 34 in close proximity and fixed to the endoscope, and hence a treatment device can be readily inserted into the opening.

According to the present invention, it is possible to provide the mucosa excising device using an endoscope by which the snare wire loop does not accidentally come off the cap at the time of insertion into a body cavity or during a treatment in the body cavity when conducting the endoscopic mucosal resection.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A mucosa excising device using an endoscope comprising:
   a snare wire having a loop portion at a distal end portion of the snare wire;
   a substantially cylindrical cap including a cylindrical wall, and a holding mechanism configured to hold the loop portion of the snare wire along an inner peripheral surface of the cylindrical wall; and
   an attachment portion which attaches the cap to an end portion of the endoscope,
   wherein the holding mechanism has a plurality of engagement pieces and a plurality of corresponding portions which are arranged along the inner peripheral surface of the cylindrical wall, and engage the loop portion to hold the loop portion of the snare wire between the engagement pieces and the corresponding portions, said plurality of engagement pieces being inwardly protruding from the cylindrical wall and being respectively distanced from each other in a circumferential direction of the cylindrical wall;
   wherein when the snare wire is drawn in a proximal direction, at least protruded ends of the engagement pieces are displaced in the proximal direction by the loop portion, thereby allowing the loop wire to be released from between the engagement pieces and the corresponding portions, so that the loop portion is disengaged from the holding mechanism.

2. The mucosa excising device using an endoscope according to claim 1, wherein at least one of each of the engagement pieces and each of the corresponding portions elastically depress the loop portion onto the corresponding portion or the engagement piece by an elastic force in a distal direction to hold the loop portion of the snare wire.

3. The mucosa excising device using an endoscope according to claim 1, wherein the cylindrical wall has an inner flange inwardly protruding from the cylindrical wall, and the engagement pieces are formed in the inner flange, each of the engagement pieces being sectioned from the corresponding portion by a pair of notches which are distanced in the circumferential direction and extended from an inner edge of the inner flange at an angle with the circumferential direction.

4. The mucosa excising device using an endoscope according to claim 3, wherein said each pair of the notches are formed to extend to the cylindrical wall through the inner flange.

5. The mucosa excising device using an endoscope according to claim 4, wherein the each of the engagement pieces is elastically deformed and caused to swivel, and the snare wire is pressed against the corresponding portion by an elastic return force of the engagement piece.

6. The mucosa excising device using an endoscope according to claim 4, wherein the corresponding portions have a flange provided to inwardly protrude from the cylindrical wall, the engagement piece has separation portions separated from each other by a notch portion formed in the inner flange, and the snare wire is supported between the flange and the separation portions.

7. The mucosa excising device using an endoscope according to claim 3, wherein the inner flange has a plurality of lateral notches extending in the circumferential direction, and said each pair of notches extend toward the cylindrical wall from both ends of each lateral notch.

8. The mucosa excising device using an endoscope according to claim 3, wherein a circular end portion of the cylindrical wall has a plurality of lateral notches extending in the circumferential direction between the inner flange and the cylindrical wall, and said each pair of notches extend toward the cylindrical wall from both ends of each lateral notch.

9. The mucosa excising device using an endoscope according to claim 3, wherein said plurality of notches include vertical notches extending at a substantially right angle.

10. The mucosa excising device using an endoscope according to claim 3, wherein said plurality of engagement pieces are arranged in the same interval in the circumferential direction.

11. The mucosa excising device using an endoscope according to claim 3, wherein each of the engagement pieces and each of the corresponding portions directly contact opposite sides of the end portion of the snare wire to hold the end portion therebetween.

12. The mucosa excising device using an endoscope according to claim 1, wherein each of the engagement pieces is movable to swivel to a side where a circular end portion of the cylindrical wall is positioned with respect to the corresponding portion, and the engagement piece holds the snare wire between its outer surface and one surface of the corresponding portion when caused to swivel.

13. The mucosa excising device using an endoscope according to claim 1, wherein the engagement pieces and the corresponding portions are alternately arranged in the circumferential direction of the circular end portion.

14. The mucosa excising device using an endoscope according to claim 1, further comprising: a snare sheath into which the snare wire is inserted; a flexible tube which has an opening on an end side, the opening communicating with the inner side of the cylindrical wall which is arranged outside the insertion portion of the endoscope when the cap is attached to the endoscope, and is used to insert the snare sheath in which the snare is inserted therethrough; and a fixture for fixing the snare sheath to prevent the snare sheath from moving in an axial direction of the snare sheath against the flexible tube, to be capable of being released, the fixture being provided in the vicinity of a base end portion of the flexible tube.

15. The mucosa excising device using an endoscope according to claim 1, wherein at least the protruded ends of the engagement pieces are deformable such that the displacement thereof is due to an elastic deformation.

16. A mucosa excising device using an endoscope comprising:
- a snare wire having a loop portion at a distal end portion of the snare wire;
- a substantially cylindrical cap having a circular end portion including a holding mechanism configured to hold the loop portion of the snare wire such that all portions of the loop portion are held interior of the circular end portion; and
- an attachment portion which attaches the cap to an end portion of an endoscope,
- wherein the holding mechanism has a plurality of engagement portions which are provided along the circular end portion of the cap and distanced from each other in a circumferential direction, and each engagement portion has an engagement piece and a corresponding portion configured to hold the loop portion of the snare wire in an elastic manner therebetween so that the loop portion is positioned to be parallel to the circular distal end portion along a circular inner surface of the cylindrical cap;
- wherein when the snare wire is drawn in a proximal direction, at least protruded ends of the engagement pieces are displaced in the proximal direction b the loop portion, thereby allowing the loop wire to be released from between the engagement portions and the corresponding portions, so that the loop portion is disengaged from the holding mechanism.

17. The mucosa excising device using an endoscope according to claim 16, wherein at least the protruded ends of the engagement pieces are deformable such that the displacement thereof is due to an elastic deformation.

* * * * *